US006290651B1

United States Patent
Chesney et al.

(10) Patent No.: US 6,290,651 B1
(45) Date of Patent: *Sep. 18, 2001

(54) VASCULAR IMPEDANCE MEASUREMENT INSTRUMENT

(75) Inventors: Charles F. Chesney, Sunfish Lake; Stanley M. Finkelstein, St. Louis Park; Jay N. Cohn, Minneapolis, all of MN (US)

(73) Assignee: Hypertension Diagnostics, Inc., Eagan, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/545,946

(22) Filed: Apr. 10, 2000

Related U.S. Application Data

(63) Continuation of application No. 09/237,444, filed on Jan. 26, 1999, now Pat. No. 6,048,318, which is a continuation of application No. 08/935,568, filed on Sep. 23, 1997, now Pat. No. 5,876,347, which is a continuation of application No. 08/228,672, filed on Apr. 18, 1994, now abandoned, which is a continuation of application No. 08/038,357, filed on Mar. 26, 1993, now Pat. No. 5,316,004, which is a continuation of application No. 07/635,278, filed on Dec. 28, 1990, now Pat. No. 5,211,177.

(51) Int. Cl.$^7$ .................................................. A61B 5/021
(52) U.S. Cl. ........................ 600/485; 483/526; 483/481
(58) Field of Search ...................................... 600/483, 481, 600/504, 526, 485; 128/920

(56) References Cited

U.S. PATENT DOCUMENTS

| | | | |
|---|---|---|---|
| 4,137,910 | 2/1979 | Murphy | 128/713 |
| 4,289,141 | 9/1981 | Cormier | 128/713 |
| 4,429,701 | 2/1984 | Goor et al. | 600/526 |
| 4,807,638 | 2/1989 | Sramek | 128/672 |
| 4,821,735 | 4/1989 | Goor et al. | 128/713 |
| 4,834,107 | 5/1989 | Warner | 128/713 |
| 4,899,758 | 2/1990 | Finkelstein et al. | 128/672 |
| 5,031,629 | 7/1991 | DeMarzo | 128/670 |
| 5,054,493 | 10/1991 | Cohn et al. | 128/672 |
| 5,103,828 | 4/1992 | Sramek | 128/668 |
| 5,241,966 | 9/1993 | Finkelstein et al. | 128/713 |
| 5,316,004 | 5/1994 | Chesney et al. | 128/672 |

OTHER PUBLICATIONS

Alderman, E.L., et al., "Evaluation of the Pulse–Contour Method of Determining Stroke Volume in Man", *Circulation*, 46, 546–558, (1972).

(List continued on next page.)

*Primary Examiner*—Kennedy Schaetzle
(74) *Attorney, Agent, or Firm*—Schwegan, Lundberg, Woessner & Kluth, P.A.

(57) ABSTRACT

A vascular impedance measurement instrument includes a transducer to obtain a digitized arterial blood pressure waveform. The digitized data is used to determine cardiac output, and to subsequently obtain measurements of impedance parameters using the modified Windkessel model of the arterial system. The instrument is used as an aid in diagnosing, treating and monitoring patients with cardiovascular disease.

12 Claims, 4 Drawing Sheets

OTHER PUBLICATIONS

Alexander, R.S., et al., "Factors Determining the Contour of Pressure Pulses Recorded from the Aorta", Federation Proceedings, 11, 738–749, (1952).

Beltran, A., et al., "Arterial Compliance Abnormality in Isolated Systolic Hypertension", Circulation. 90, 67th Scientific Sessions of the American Heart Assn., Abstract No. 2726, I–506, (Oct. 1994).

Beltran, E.L., et al., "A Non–Invasive Method for Measuring Regional Peripheral Compliance", IEEE Engineering in Medicine and Biology Society Proceedings, 11, 134–135, (1989).

Boehmer, R.D., "Continuous, Real–Time, Noninvasive Monitor of Blood Pressure: Penaz Methodology Applied to the Finger", J. of Clin. Monitoring, 3(4).

Bourgeois, M.J., et al., "Characteristics of Aortic Diastolic Pressure Decay with Application to the Continuous Monitoring of Changes in Peripheral Vascular Resistance", circulation Research, 35, 56–66, (1974).

Bourgeois, M.J., et al., "continous Determination of Beat–to–Beat Stroke Volume from Aortic Pressure Pulses in the Dog", Circulation, 39, 15–24, (1976).

Braunwald, E., et al., "Determinants of Duration and Mean Rate of Ventricular Ejection", Circulation Research, 6, 319–325, (1958).

Cardus, D., et al., "Systolic Time Intervals at Rest and During exercise", Cardiology, 59, 133–153, (1974).

Caro, C.G., et al., "The Mechanics of the Circulation", Oxford Medical Publications, 268–278, (1978).

Cinelli, P., et al., "Systolic Time Intervals During Isometric Exercise in Supine Position Should be Corrected Also for Arterial Pressure", Acta Cardiological, 37(2), 93–103, (1982).

Cohn, J.N., "Drugs Used to Control Vascular resistance and Capacitance", In: The Heart, Schlant, R. (ed.), 8th Ed., (1993).

Cohn, J.N., "Evaluation of Arterial Compliance", In: Hypertension Primer, Izzo, J.L. and Black, H.R., (eds.), Pub. By Council on High Blood Pressure Research, American Heart Association, pp. 252–253, (1993).

Cohn, J.N., "Functional Impact of Structural or Tone Changes in Small and Large Arteries", The Atherosclerotc Blood Vessel, Structural and Functional Assessment of the Atherosclerotc Blood Vessel, San Francisco, Jul. 1993, 15–16, (1993).

Cohn, J.N., "Methods of Evaluation of Arterial Compliance", Hypertension Primer, J.L. Izzo et al. (eds.) Published by Council on High Blood Pressure Research, American Heart Association, 252–253, (1993).

Cohn, J.N., "Pharacologic Mechanisms of Nitrates in Myocardial Ischemia", American Journal of cardiology, 70, 38G–42G, (Nov. 1992).

Cohn, J.N., "Structural Changes in Cardiovascular Disease", Am. J. Cardiol., 76, 34E–37E, (1995).

Cohn, J.N., "The Role of Vascular Compliance in Abnormalities of Hypertension and Atherosclerosis", Atherosclerosis Beyond Cholesteral, Monograph from Proceedings of a Symposium by the Council on Hypertension and Atherosclerosis Education, La Quinta, CA, Jan., 1991, 55–60, (1992).

Cohn, J.N., et al., "Abnormalities of Vascular Compliance in Hypertension, Aging and Heart Failure", Journal of Hypertension, 10 (Suppl. 6), Abstract and Presentation at the Int'l Soc. of Hypertension Workshop on Arterial Compliance, "Functional and Structural Properties aof Large Arteries", Paris, Mar. 6–7, 1992, S61–S64, (1992).

Cohn, J.N., et al., "Measurement of Vascular Compliance as a Guide to Vasoconstrictor and Vasodilatior Stimuli", Blood Vessels, 20, 189, (1983).

Cohn, J.N., et al., "Noninvasive Pulse wave Analysis for the early detection of Vascular Disease", Hypertension, 26, 503–508, (Sep. 1995).

Cohn, J.N., et al., "Vascular Complaince in Heart Failure: A Contributor to Impedance, and the Response to Vasodilator Drugs", In: Heart Failure Mechanisms and Management, B. S. Lewis and A. Kimchi, (eds.), Springer–Verlag, N.Y., 1991, pp. 42–44.

Collins, V.R., et al., "Evaluation of a Pulse Contour Technique for Measuring Arterial Elasticity", Circulation, 62, suppl. II, III–1120, (1980).

Cundick, Jr., R.M., et al., "Clinical Comparison of Pressure–Pulse and Indicator–Dilution Cardiac Output determination", Circulation, 62, 371–376, (1980).

Ekman, L.G., et al., "Clinical Evaluation of an Ensemble–Averaging Impedance Cardiograph for Monitoring Stroke Volume During Spontaneous Breathing", Acta Anaesthesiol Scand, 34, 199–196, (1990).

English, J.B., et al., "Comparison of Aortic Pulse–Wave contour Analysis and Thermodilution Methods of Measuring Cardiac Output During Anesthesia in Dog", Anesthehsiology, 52, 56–61, (1981).

Feske, W., et al., "Arterial Vascular Compliance Response to Excercise in Hypertension", Biomedical Sciences Instrumentation, 24, 161–165, (1988).

Feske, W., et al., "Reduced Arterial Compliance in Hypertension", Hypertension, 12, Presented at High Blood Pressure Research Council (Amer. Heart Assn.) meeting in san Francisco, Sep. 1988, 343.

Feske, W., et al., "Vascular Compliance after Nitroprusside in Hypertension", IEEE Proceedings, 14, 14th Annual N.E. Bioengineer. Symp., 277–280, (1988).

Finkelstein, S.M., "Compliance Measurements Using Pulse Wave Analysis", The Atherosclerotic Blood Vessel, Structural and Functional Assessment of the Atherosclerotic Blood Vessel, San Francisco, Jul. 1993, 32–33, (1993).

Finkelstein, S.M., et al., "A Comparison of Invasion and Non–Invasive Blood Pressure Measurements for Determining Arterial Vascular Compliance", Proccedings of the Annual Int'l. Conference of the IEEE Engineering in Medicine and Biology Society, 13, 2073–2074, (1991).

Finkelstein, S.M., et al., "Arterial Vascular Compliance in Heart failure", IEEE Engineering in Medicine and Biology Society Proceedings, 12, 548–549, (Nov. 1990).

Finkelstein, S.M., et al., "Arterial Vascular Compliance Response to Vasodilators by Fourier and Pulse Contour Analysis", Hypertension, 12, 380–387, (1988).

Finkelstein, S.M., et al., "Assessment of Vasodilators in the Time and frequency Domains", Update in Cardiac Surgery, Anesthesia and Intensive Care, 2nd International Symposium, Ghent, Sep. 21–24, 1993, 47–49, (1993).

Finkelstein, S.M., et al., "Determining Stroke Volume from Arterial Blood Pressure Contour Analysis", Clinical Research, 40, 438A, (1992).

Finkelstein, S.M., et al., "Evidence for Abnormal Vascular Compliance by Pulse Contour Analysis in Congestive Heart Failure", *Circulation*, 66, Suppl. II, 1109, (1982).

Finkelstein, S.M., et al., "First and Third–Order Models for Determining Arterial Compliance", *Int'l. Soc. Hypertension Workshop on Arterial Compliance, Functional and Structural Properties of Large Arteries*, Paris, Mar. 6–7, 1992, Abstract.

Finkelstein, S.M., et al., "First and Third–Order Models for Determining Arterial compliance", *Journal of Hypertension*, 10 (Suppl. 6), S11–S14, (1992).

Finkelstein, S.M., et al., "Impedance Response to Nitroprusside in Heart failure", Proceedings Engineering in Medicine and Biology, 26, 37th Annual Conf., 259, (1984).

Finkelstein, S.M., et al., "Reproducibiliy of Vascular Compliance Measurements", IEEE Engineering in Medicine and Biology Society Proceedings, 11, 116–117, (1989).

Finkelstein, S.M., et al., "Response of Vascular Compliance to Converting Enzyme Inhibitors in Heart Failure", A.A.M.I. Proceed., 20, 29, (1985).

Finkelstein, S.M., et al., "Selective Effects of Left Ventricular Failure and Aging on Vascular Compliance", *Circulation*, 82, Suppl. III, III–4000, (1990).

Finkelstein, S.M., et al., "Vascular Compliance in Congestive Heart Failure", Proceedings of the 7th Annual Conf. (Chicago, Il) of the IEEE Engineering in Medicine and Biology Society, 7, 550–553, (1985).

Finkelstein, S.M., et al., "Vascular Compliance in Hypertension", IEEE Engineering in Medicine and Biology Society, 10, 10th Annual Int'l. Conf. Proceed., 241–242, (1988).

Finkelstein, S.M., et al., "Vascular Compliance Response to Converting Enzyme Inhibitors in Heart Failure", *Circulation*, 76, (Suppl. 4), 178, (1987).

Finkelstein, S.M., et al., "Vascular Hemodynamic Impedance in Congestive Heart Failure", *American Journal of Cardiology*, 55, 423–427, (1985).

Finkelstein, S.M., et al., "Vascular Hemodynamic Impedance Measurement Methods", *Progress in Cardiovascular Disease*, 24, 401–418, (1982).

Finkelstein, S.M., et al., "Vascular Impedance by Pulse–Contour/Windkessel Analysis", A.A.M.I. Proceed., 19, 27, (1984).

Finkelstein, S.M., et al., "Vascular Impedance in Health, Hypertension, and Heart Failure", Proceedings Engineering in Medicine and Biology, 25, 36th Annual Conf., 202, (1983).

Finkelstein, S.M., et al., "Vascular Impedance Methodology in Congestive Heart Failure", Alliance of Engineering in Medicine and Biology Proceedings, 24 , 35th Annual Conf., 143, (1982).

Finkelstein, S.M., et al., "Vascular Impedance Response to Vasodilator Drugs", Alliance of Engineering in Medicine and Biology Proceedings, 23, 346, (1981).

Finkelstein, S.M., et al., "Vascular Effects On Vascular Impedance Characteristics", Federation Proceedings, Part II of 3, vol. 38, No. 3 from 63rd Annual Meeting 4–1–79, 991, (1979).

Goldwyn, R.M., et al., "Arterial Pressure Pulse Contour Analysis Via a mathmatical Model for the Clinical Quantification of Human Vascular Properties", *Transacation on Biomedical Engineering*, BME–14(1), (1967).

Haidet, G.C., et al., "Effects of Aging on Arterial Compliance in the Beagle", *Clinical Research*, 40, 266a, (1992).

Harley, A., et al., "Pressure–Flow Studies in Man. An Evaluation of the Duration of the Phases of the Systole", *The Journal of Clinical Investigation*, 48, 895–905, (1969).

Herd, J.A., et al., "Arterial Pressure Pulse Contours During Hemorrahage in Anesthetized Dogs", *J. Appl. Physiol.*, 21, 1864–1868, (1966).

Holmgren, A., et al. "Circulatory Data in Normal Subjects at Rest and During Exercise in Recumbent Position, with Specific Reference to the Stroke Volume at Different Work Intensities", *Acta Physiol. Scand.*, 49, 343–363, (1966).

Holvey, D.N., et al., *The Merck Manual of Diagnosis and Therapy, 12th Edition*, Reproduced from W. Brothby and R. B. Sandford, Boston Medical and Surgical Journal, vol. 185, p. 337, 1921, p. 1840, (1972).

Kouchoukos, N.T., et al., "Estimation of Stroke Volume in the Dog by a Pulse Contour Method", *Circulation Research*, 26, 611–623, (1960).

Krovetz, L.J., "Normal Standards for Cardiovascular Data I. Examination of the Validity of Cardiac Index", *John Hopkins Medical Journal*, 130 (3), 174–186, (1972).

Lompard, W.P., et al., "Effect of Posture on the Lenght of the Systole of the Human Heart", *Am. J. Physiol.*, 40, 140–141, (1919).

McDonald, D.A., *Blood Flow in Arteries*, Williams & Wilkins Co., Baltimore, pp. 258–281, (1960).

McVeigh, G., et al., "Vascular Abnormalities in Non–Insulin Dependent Diabetes Mellitus Indentified by Arterial Waveform Analysis", *American Journal of Medicine*, 95, 424–430, (Oct. 1993).

McVeigh, G.E., et al., "Assessment of Arterial Compliance in Hypertension", *Current Opinion in Nephrology and Hypertension*, 2, 82–86, (1993).

McVeigh, G.E., "Effects of Long–Term Cigarette Smoking on Endothelium–Dependent Responses in Humans", *Am. J. of Cardiology*, 78, 668–672, (1996).

McVeigh, G.E., et al., "Fish oil improves Arterial Compliance in Non–Insulin Dependent Diabetes Mellitus", *Arteriosclerosis and Thrombosis*, 14, 1425–1429, (Sep. 1994).

McVeigh, G.E., et al., "Influence of Age and Blood Pressure on Vascular Compliance", *American J. Hypertension*, 12, Abstract Presented at the 4th Scientific Meeting of the Amer. Soc. Hypertension, New York, May, 1989, Abstract No. 72A, (1989).

McVeigh, G.E., et al., "Reduced Vascular Compliance as a Marker for essential Hypertension", *American Journal of Hypertension*, 4, 245–251, (1991).

McVeigh, G.E., et al., "Vascular Compliance", *In: Cardiovascular Medicine*, Wllerson, J.T. and Cohn, J.N. (eds.), Churchill Livingstone, Inc., New York, Nov. 1994, 1212–1227.

McVeigh, G.E., et al., "Vascular Compliance in Essential Hypertension", *Circulation (Suppl. II)*, 80, II–594, (1989).

Mock, J.E., et al., "Vascular Compliance Changes During the Progression of Hypertension in Dogs", *Hypertension*, 12, Presented at the High Blood Pressure Research Council (Amer. Heart Assn.) meeting in San Francisco, Sep. 1988, 360.

Mock, J.E., et al., "Vascular Compliance Changes in Hypertensive Dogs After Nitroprusside Infusion as Measured by Pulse Contour Analysis", *Biomedical Sciences Instrumentation*, 23, 77–82, (1987).

Mock, J.E., et al., "Vasoconstrictor Drug Effects on Vascular Compliance by Pulse Contour Analysis", IEEE Engineering in Medicine and Biology Society Proceedings, 9, 878–880, (1987).

Mock, J.E., et al., "Vasoconstrictor Mediated Reduction in Vascular Compliance Assessed by Pulse Contour Analysis", *Circulation,* 76 (Suppl. 4), 441, (1987).

Neutel, J.M., et al., "Dependency of Arterial Compliance on Circulating Neuroendocrine and Metabolic Factors in Normal Subjects", *American Journal of Cardiology,* 69, 13401344, (May, 1992).

Ohmeda Literature, "With the Finapres Continuous NIBP Monitor, the Pressure is Always On".

Opdyke, D.F., "Genesis of the Pressure Pulse Contour Method for Calculating Cardiac Stroke Index", Federal Proceedings, 11, 733–737, (1952).

Remington, J.W., "Volume Quantitation of the Aortic Pressure Pulse", Federation Proceedings, 11, 750–761, (1952).

Remington, J.W., et al., "Formation of Peripheral Pulse Contour in Man", *J. Appl. Physiol.,* 9, 433–442, (1956).

Smith, D.G., et al., "The Relationship of Arterial Compliance with Endothelial–Derived Proteins of the Hemostatic System", *Life Sciences,* 52, 1005–1011, (1993).

Smulyan, H., et al., "An Evaluation of the Cardiac Index", *American Heart Journal,* 72, (S): 621–31.

Spencer, M.P., et al., "Pulsatile blood flow in the vascular system", *Handbook of Physiology,* Section 2, vol. 2, pp. 839–864, (1963).

Spodick, D.B., et al., "Systolic Time Intervals Reconsidered. Reevaluation of the Preejection Period: Absence of Relation to Heart rate", *The American Journal of Cardiology,* 53, 1667–1670, (1984).

Starmer, C.F., et al., "Evaluation of Several Methods for Computing Stroke Volume from Central Aortic Pressure", *Circulation Research,* 33, 139–148, (1973).

Stefadouros, M.A., et al., "The Effect of Isometric Exercise on the Left Ventricular Volume in Normal Man", *Circulation,* 49, 1185–1189, (1974).

Tajimi, T., "Evaluation of Pulse Contour Methods in Calculating Stroke Volume from Pulmonary Artery Pressure Curve (Comparison with Aortic Pressure Curve)", *European Heart Journal,* 4, 502–511, (1983).

Wallace, A.G., et al., "Duration of the Phases of Left Ventricular Systole", *Circulation Research,* 12, 611–619, (1963).

Warner, H.R., et al., "Computer–Based Monitoring of Cardiovascular Functions in Postoperative Patients", *Circulation,* 37 (Suppl. II), II–68–II–74, (1968).

Warner, H.R., et al., "Quantitation of Beat–to–Beat Changes in Stroke Volume From the Aortic Pulse Contour in Man", *J. Appl. Physiol.,* 5, 495–507, (1953).

Warner, H.R., et al., "The Role of Computers in Medical Research", *JAMA,* 196(11),126–131, (1966).

Watt, T.B., et al., "Arterial Pressure Contour Analysis for Estimating Human Vascular Properties", *Journal of Applied Physiology,* 171–176, (1976).

Weber, M.A., "Hypertension as a Multiple Risk Factor Syndrome oand Implications for Antihypertensive Therapy", *Atherosclerosis Beyond Cholesterol,* Proceedings of a Symposium by the Council on Hypertension and Atherosclerosis Education, La Quinta, CA, Jan. 1991, 61–71, (1991).

Weber, M.A., et al., "Arterial Properties of Early Hypertension", *Journal of Human Hypertension,* 5, 417–423, (1991).

Weber, M.A., et al., "Cardiovascular and metabolic Characteristics of Hypertension", *American Journal of Medicine,* 91, Suppl. 1A, 4S–10S, (Jul. 1991).

Weissler, A.M., et al., "Relationships Bewteen Left Ventricular Ejection Time, Stroke Volume, and Heart Rate in Normal Individuals and Patients with Cardiovascular Disease", *Am. Heart J.,* 62, 367–378, (1961).

Weissler, A.M., et al., "Systolic Time Intervals in Heart Failure in man", *Circulation,* 37, 149–159, (1968).

Willems, J., et al., "The Left Ventricular Ejection Time: Its Relation to Heart Rate, Mechanical Systole and Some Anthropometric Data", *Acta Cardiological,* 22, 401–425, (1967).

Yaginuma, T., et al., "Introduction to wave Reflection, Wave Travel and Changes with Modification of Geometric and Physical Parameters", *Journal of Hypertension, Suppl.* 10, 6, S71–72, (Aug. 1992).

Zobel, L.R., et al., "Pressure Pulse Contour Analysis in Determining the Effect of Vasodilator Drugs on Vascular Hemodynamic Impedance Characteristics in Dogs", *American Heart Journal,* 100, 81–88, (1980).

Zobel, L.R., et al., "Vasodilator Effects on Vasular Impedance Characteristics", Fed. Proceed., (1979).

$C_1$ = PROXIMAL ARTERIAL COMPLIANCE (ml/mm Hg);

$C_2$ = DISTAL ARTERIAL COMPLIANCE (ml/mm Hg);

L = INERTENCE (mm Hg/ml/s(2));

$P_1$ = PROXIMAL ARTERIAL (AORTIC) PRESSURE (mm Hg);

$P_2$ = DISTAL ARTERIAL (BRACHIAL) PRESSURE (mm Hg); AND

R = PERIPHERAL RESISTANCE (DYNES s $cm^{-5}$).

VASCULAR IMPEDANCE MEASUREMENT INSTRUMENT

This application is a continuation of U.S. Ser. No. 09/237,444 filed Jan. 26, 1999 and now U.S. Pat. No. 6,048,318, which is a continuation of U.S. Ser. No. 08/935,568 filed Sep. 23, 1997 and now U.S. Pat. No. 5,876,347, which is a continuation of U.S. Ser. No. 08/228,672, filed Apr. 18, 1994 and now abandoned, which is a continuation of U.S. Ser. No. 08/038,357 filed Mar. 26, 1993 and now U.S. Pat. No. 5,316,004, which is a continuation of U.S. Pat. No. 07/635,278, filed Dec. 28, 1990 and now U.S. Pat. No. 5,211,177.

TECHNICAL FIELD OF THE INVENTION

The present invention pertains generally to the field of cardiovascular medicine, and more particularly, to an instrument for characterizing the status of the cardiovascular system using an electrical analog model thereof.

BACKGROUND OF THE INVENTION

The modified Windkessel electrical analog model of the arterial system is gaining increasing attention from the medical community as a clinically useful tool for characterizing the human vasculature for the purpose of diagnosing, treating and monitoring cardiovascular disease. A number of studies of the cardiovascular system using the modified Windkessel model have been conducted, and correlations between the model parameters and normal and disease states have been identified. For instance, U.S. patent application Ser. No. 07/250,315, entitled "Method for Diagnosing Hypertension," discloses a method for utilizing the parameter $C_2$ of the modified Windkessel model to diagnose, treat and monitor the vascular disease condition underlying hypertension.

The modified Windkessel model of the arterial system is shown in FIG. 1. In the model:

$C_1$=proximal arterial compliance (ml/mm Hg);

$C_2$=distal arterial compliance (ml/mm Hg);

L=inertence (mm Hg/ml/s$^2$);

$P_1$=proximal arterial (aortic) pressure (mm Hg);

$P_2$distal arterial (brachial) pressure (mm Hg); and

R=peripheral resistance (dynes sec cm$^{-5}$).

While the usefulness of the Windkessel model parameters for the diagnosis, treatment and monitoring of cardiovascular disease has become more apparent, they remain relatively difficult to use on a routine basis for two reasons. The first is the need to obtain a cardiac output measurement in order to determine the parameters. Conventional procedures for determining cardiac output, such as thermodilution and dye dilution, are surgically invasive, requiring catheterization of the patient. Physicians, in general, are reluctant to employ such procedures because of their cost, the discomfort and inconvenience to the patient, the risk of infection and other severe complications, and their relative level of complexity as compared to alternative noninvasive procedures. The second reason involves the difficulty with obtaining patient data for the modified Windkessel model from blood pressure waveforms, which also conventionally requires the insertion of an arterial catheter and the use of a transducer and other electronic equipment.

The present invention, as described hereinafter, provides an instrument which can noninvasively measure Windkessel parameters, or other impedance parameters which depend on cardiac output measurement, using a noninvasively obtained arterial blood pressure waveform of the patient. Accordingly, it is contemplated that the present invention will significantly facilitate widespread clinical use of the modified Windkessel model parameters, or other impedance model parameters, in the diagnosis, treatment and monitoring of cardiovascular disease. In particular, the invention allows for a quick, easy-to-use and noninvasive determination of the modified Windkessel parameters so that these parameters can be ascertained and used during routine physical examinations, and patient screening, treatment and monitoring. Given that the only existing practical and quick screening device for determining the status of the cardiovascular state is a blood pressure cuff (i.e., a sphygmomanometer) measurement, it is contemplated that the invention could provide a substantial and new diagnostic capability for physicians to use on a routine basis.

SUMMARY OF THE INVENTION

The present invention provides a vascular impedance parameter instrument comprising transducer means for converting a noninvasively obtained arterial blood pressure waveform signal to a corresponding analog electrical signal, means for digitizing the analog signal, means for processing the digitized signal and determining a cardiac output value based on characteristics of the arterial blood pressure waveform and on other noninvasively determined patient data, and means for utilizing the cardiac output value and for further processing of the waveform signal in order to determine one or more vascular impedance parameter measurements. The present invention recognizes that usable and useful Windkessel parameter measurements can be obtained even if the cardiac output value used to obtain the measurements are not particularly accurate. Accordingly, the present invention provides that cardiac output measurements be obtained noninvasively, using the same arterial blood pressure waveform used to obtain the Windkessel model parameter measurements.

DETAILED DESCRIPTION OF THE INVENTION

Figure 2:
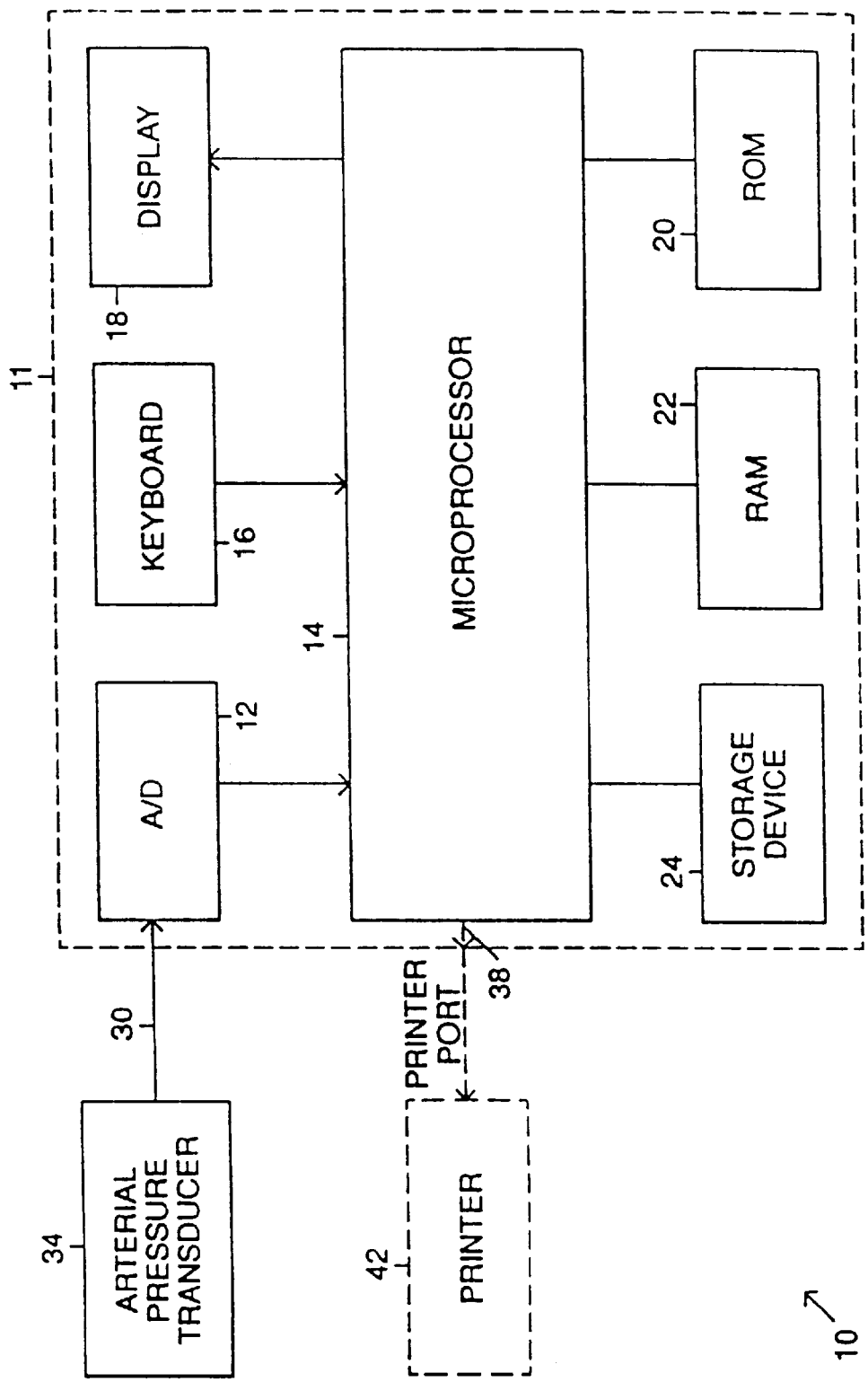
FIG. 2 is a schematic block diagram of the modified Windkessel parameter vascular impedance measurement instrument according to the present invention.

The modified Windkessel parameter vascular impedance measurement instrument 10 according to the present invention is shown in simplified schematic block diagram form in FIG. 2. The instrument 10 includes a transducer unit 34, a computer system 11, and optionally a printer 42. System 11 includes an analog to digital convertor (A/D) 12, preferably 12-bit, and a microprocessor unit 14, for instance a model 80386 by Intel, a keyboard input 16, a display 18, a ROM 20, a RAM 22 and a storage device 24. An input port 30 is provided to receive analog signal input from an arterial pressure transducer unit 34. Microprocessor 14 includes an output port 38 connected to optional printer 42.

Transducer unit 34 is preferably a noninvasive arterial blood pressure waveform measurement device, for example, a finger-cuff transducer unit using a counter pulsation technique wherein the waveform is detected by balancing the air pressure in a finger cuff with the blood pressure in the patient's finger. A commercially available finger-cuff transducer unit of this type is the Finapres® Continuous NIBP Monitor model 2300, from Ohmeda Monitoring Systems division of the BOC Group, Inc., 355 Inverness Drive South, Engelwood, Colo. 80112-5810. The Finapres® device produces an analog output signal which is fed through port 30 to A/D converter 12. Another noninvasive transducer unit available for use with the present invention is the Model 506 Non-Invasive Patient Monitor from Criticare Systems, Inc., 20900 Swenson Drive, Suite 398, Waukesha, Wis. 53186. A third commercially available transducer unit is the Model CMB-7000 from Nellcor Incorporated, 25495 Whitesell Street, Hayward, Calif. 94545. This unit noninvasively measures arterial blood pressure and provides waveform data based on the technique of arterial tonometry. It is also contemplated that the measured waveform may be transformed in digital form from the transducer unit 34 directly to the microprocessor 14, avoiding the need for A/D converter 12.

The arterial waveform may also be obtained invasively, if desired, although this is not believed to be preferred from a cost, medical risk and patient convenience perspective, using a Statham P23Db pressure transducer as unit 34. If obtained invasively, preferably, such a transducer would be connected to a patient's brachial artery via an 18-gauge, 2-inch Teflon catheter. This catheter-transducer system has an undamped natural frequency higher than 25 HZ and a damping coefficient less than 0.5, providing an acceptable frequency response. It shall be understood, however, that while the brachial artery is preferred, other peripheral arterial locations for obtaining the blood pressure waveforms can be substituted.

Figure 3:
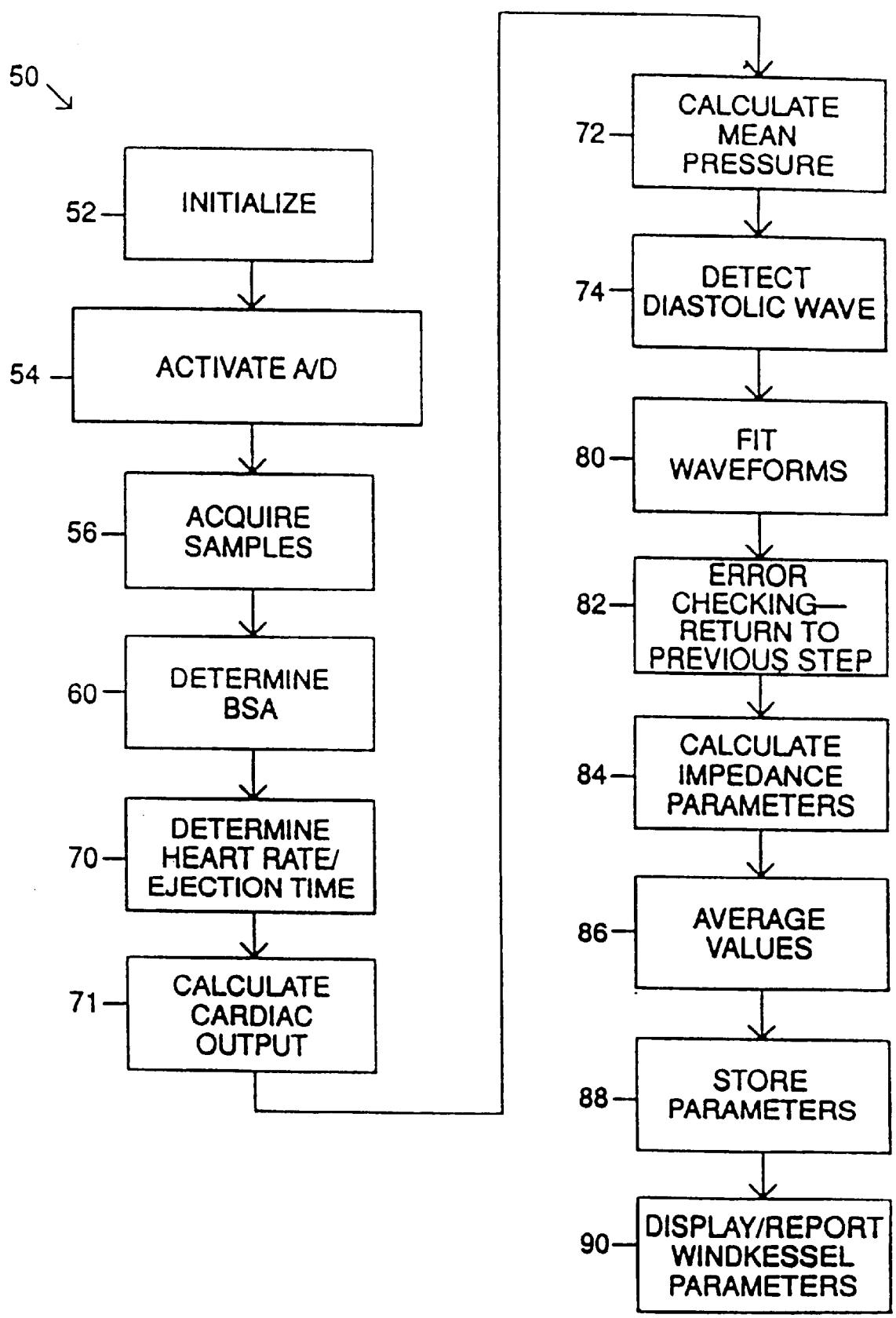
FIG. 3 is a schematic flow chart of the software components of the present invention.

The software component 50 of the invention is illustrated in block diagram flow-chart form in FIG. 3. Software 50 is preferably stored in ROM 20 or storage device 24, and is referenced by microprocessor 14. Storage device 24 can be a hard disk, floppy disk or other digital storage system.

Figure 4:
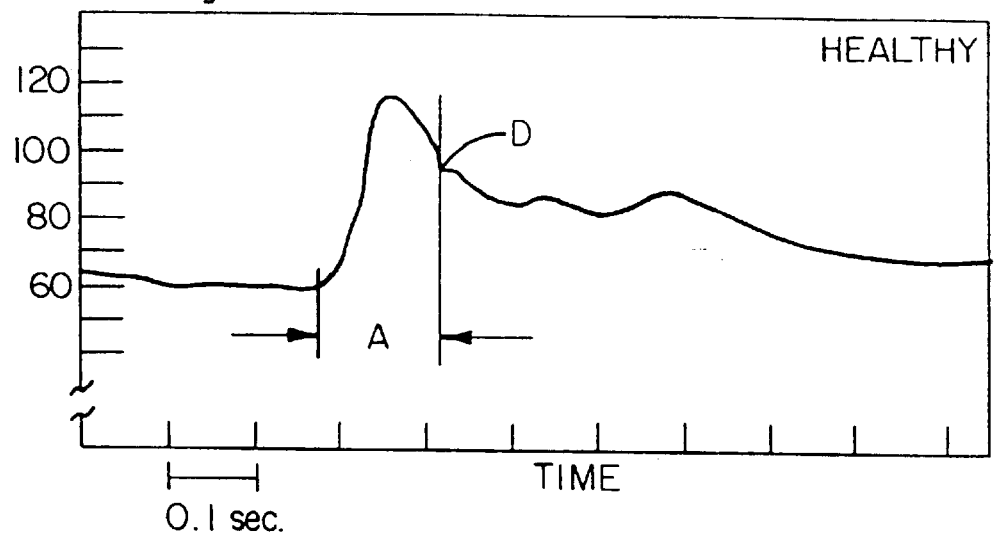
FIG. 4 is an illustrative example of a typical arterial blood pressure pulse contour or waveform in a healthy patient with the systolic ejection time marked as segment A.
Figure 5:
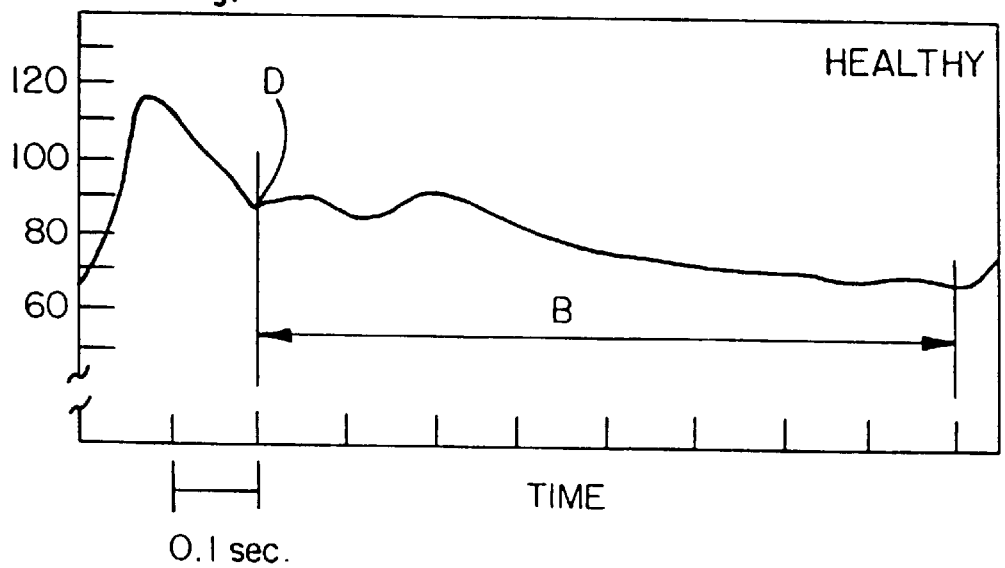
FIG. 5 is an illustrative example of typical arterial blood pressure pulse contour or waveform in a healthy patient with the diastolic decay time of the waveform marked as segment B.

Software 50 runs on microprocessor 14 to control the acquisition of arterial blood pressure waveform data, and to perform other instrument functions, as described below. An initialization and mode select routine 52 is provided for initializing microprocessor 14, including prompting the user to enter patient information, including the patient's age, height, weight, and/or body surface area. Routine 52 further provides that the waveform measurement process may be activated. If activated, A/D convertor 12 is activated (54) to digitize an analog blood pressure waveform signal generated by transducer 34. (Alternatively, as noted above, microprocessor 14 could obtain the pressure pulse measurements in digital form directly from transducer unit 34, it available, without the use of digitizer 54). FIGS. 4 and 5 illustrate typical arterial blood pressure waveforms for healthy patients.

The present invention uses an A/D sampling rate of 200 samples/second, which is satisfactory to capture the highest frequency components of interest in the arterial blood pressure waveform. It shall be understood, however, that higher or lower sampling rates may be used, and that the invention is in no way limited to the 200 samples/second rate. Routine 56 provides that the waveform data is sampled for approximately 30 seconds, producing in the range of 25 to 60 digitized arterial pulses, depending on the heart rate. The stream of digitized pulses are stored in RAM 22 or device 24 in the form of a continuous series of periodic time dependent data byte samples, with each data byte corresponding to the instantaneous pressure of the artery.

Routine 60 determines body surface area by standard formula, or alternatively, looks it up in a nomogram table stored in memory, using the patient's height and weight data. Alternatively, body surface area (BSA) can be determined by the physician or other care giver and entered directly into the instrument at routine 52, as noted above. A formula for determining BSA known to work in connection with the present invention is:

$$BSA\ (m^{-2}) = 0.0072 \times weight^{0.425} \times height^{0.725}$$

where
weight is in kilograms and height is in centimeters.

A nomogram table known to work with the present invention is found in the Merck Manual, 12th edition, 1972 on page 1840 (reproduced from Wm. Brothby and R. B. Sandford, Boston Medical and Surgical Journal, Vol. 185, page 337, 1921).

Routine 70 performs three functions: (1) it selects consecutive heart beats; (2) determines the heart rate; and (3) determines the systolic ejection time of the heart.

First, routine 70 selects a group of consecutive representative beats (it has been found that six to ten beats are preferred, but the number used is in no way critical to the invention) preferably of comparatively low noise content. Representative beats are identified by establishing windows of permissible heart rate and mean arterial pressure values whereby abnormally fast or slow heartbeats, or high or low pressures can be rejected. The routine can thus pick the series of beats which is most representative.

Second, the heart rate (HR) is also determined by routine 70, by counting the number of beats per unit time. Where possible, it is preferable that the windows be tailored to the patient, thus allowing more precise selection of representative heart beats.

Thirdly, routine 70 determines systolic ejection time as follows. First, the arterial blood pressure waveforms are marked for analysis. When marked manually, a clinician can identify the onset of systole by the initial upstroke of arterial pressure. The end of systole, which is the onset of diastole, can be found manually by correlating to the second heart sound $S_2$, or by identifying the dicrotic notch on the arterial pressure wave. Ejection time is then determined by the time between the onset of systole and the beginning of diastole. For example, in FIG. 4, systolic ejection time is marked by segment A assuming a waveform obtained in the root of the aorta.

The present invention uses a software analysis algorithm at routine 70 to predict and select the segment A for each pressure waveform most probably corresponding to ejection time. Routine 70 searches the waveform data for the waveform upstroke marking systole, and then for the dicrotic notch (D), looked for after the peak of the systolic upstroke, and marks the onset of diastole just before the location of the dicrotic notch on the waveform. The ejection time (ET) is then determined from the location of the onset of systole and diastole. Transit time effects due to the distance between the proximal aorta and the arterial measurement site are taken into account in the ejection time measurement by moving back a predetermined interval (depending on where the arterial waveform is obtained in the arterial system) from the trough of the dicrotic notch to determine the end of systole for the purposes of the ejection time determination. The ejection time is thus the time between the upstroke (beginning of systole) and this point marking the end of systole. For waveforms obtained from the femoral or brachial artery, an interval of about 25 milliseconds has been found satisfactory to compensate for transit time effects. Shorter or longer intervals would be appropriate for waveforms obtained closer to or further from the heart, respectively.

Alternatively, instrument 10 can include means for digitizing an analog signal representing the heart sounds, software for identifying the first and second heart sounds $S_1$ and $S_2$, and for correlating them to the digitized arterial waveform to identify the onset of systole and diastole.

Routine 71 calculates stroke volume (SV) using the heart rate (HR), body surface area (BSA), ejection time (ET) and age for the subject, according to the following formula:

$$SV=-6.6+(0.25 \times ET)+(40.4 \times BSA)-(0.51 \times Age)-(0.62 \times HR),$$

where

SV equals stroke volume in ml/beat,

ET is ejection time in msec,

BSA is body surface area in square meters,

Age is expressed in years, and

HR is heart rate in beats per minute.

Once SV is known, cardiac output can be determined by multiplying heart rate (HR) times stroke volume (SV).

As illustrated in copending application Ser. No. 07/601,460, filed Oct. 23, 1990 and entitled "Method and Apparatus for Measuring Cardiac Output," hereby incorporated herein by reference, the cardiac output values obtained by the above-described system are relatively accurate. In approximately 90% of known cases the measurements have been within plus or minus 25% of the measurement obtained using a so-called "Gold Standard" thermodilution or dye dilution technique. This accuracy compares quite favorably against the 15–20% reproducibility of these dilution techniques.

It is currently contemplated that the formula for determining cardiac output set forth herein will be further refined and adjusted as additional data are collected and/or as adjustments to constants and factors are determined to produce more accurate determinations of cardiac output. The formula may be adjusted by performing a multiple linear regression to fit a new formula on "Gold Standard" data. Also, the particular formula set forth herein is not essential to the Windkessel parameter vascular impedance measurement instrument of the present invention. Other formulas and/or approaches to obtaining cardiac output neasurements using the blood pressure waveform can be substituted for the particular formula set forth herein, provided that they give a reasonable degree of accuracy of measurement. References to other possible substitute approaches are given in the above-referenced application Ser. No. 07/601,460.

A routine 72 is provided to calculate the mean arterial pressure utilizing the blood pressure waveform data. The mean pressure value is used, as described herein, to determine the modified Windkessel parameters. With a cardiac output and mean arterial pressure value, the modified Windkessel parameters may be determined. To ascertain the modified Windkessel variables, the diastolic portion (i.e. that part of the pressure wave which corresponds to the period of diastole in the heart) of each selected beat must be identified and a routine 74 is provided for this purpose.

When marked manually, a clinician can identify the onset of diastole by correlating the second heart sound $S_2$ and the end of diastole by the upstroke of the following pulse. For example, in FIG. 5, diastole is marked by the segment B. However, for the sake of speed and simplicity, the present invention uses a software analysis algorithm to predict and select the segment in each pressure waveform most probably corresponding to diastole. Precise detection of onset is generally not critical because the slope of the pulse wave is generally uniform in the range of diastole onset. It is, however, important that the onset of the diastolic waveform to be used occur after the peak of systole and preferably within twenty milliseconds after the dicrotic notch (D). Thus, routine 74 searches the digital waveform representation for the dicrotic notch and marks the onset of diastole immediately thereafter on the waveform. The end of diastole in the waveform is easily located by finding the upstroke of the next pulse. With the relevant waveform segments so marked, the data for each pressure waveform can be analyzed to reveal the Windkessel vascular impedance properties of the patient.

Figure 1:
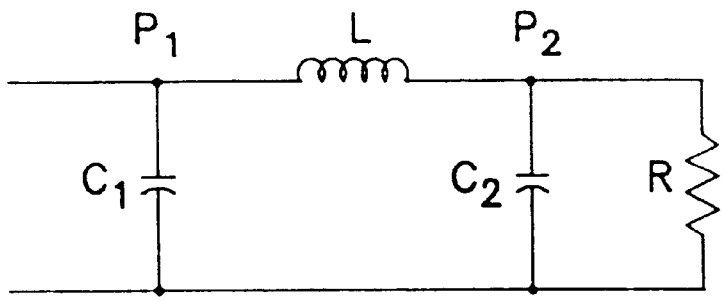
FIG. 1 is a circuit diagram of a modified Windkessel model of the vascular circulation.

The modified Windkessel model of the arterial system is used in the pulse contour analysis of the present invention. As shown in FIG. 1, the model includes components $P_1$, $P_2$, $C_1$, $C_2$, L and R in which:

$C_1$=proximal compliance (ml/mm Hg)

$C_2$=distal compliance (ml/mm Hg)

L=inertence (mm Hg/ml/s$^2$)

$P_1$=proximal arterial pressure (mm Hg)

$P_2$=brachial artery pressure (mm Hg)

R=peripheral resistance (dynes s cm$^{-5}$)

As taught, for example, by Goldwyn and Watt in I.E.E.E. Trans. Biomed. Eng. 1967; 14:11–17, the disclosure of which is hereby incorporated by reference herein, $P_2$ of the modified Windkessel model may be represented by the third order equation:

$$P_2(t)=A_1 \exp(-A_2 t)+A_3 \exp(-A_4 t) \cos(A_5 t+A_6),$$

wherein:

$$C_1 \frac{mn-p}{mp} \frac{1}{R}$$

$$C_2 = \frac{1}{m} \frac{1}{R}$$

$$L = \frac{m^2 R}{mn-p} \text{ and}$$

wherein:

$m=A_2+2A_4$ $n=2 A_2 A_4+A_4^2+A_5^2$ and $p=A_2(A_4^2+A_5^2)$

Thus, knowing R, which can be calculated from cardiac output and mean arterial pressure as follows:

$$R = \frac{\text{mean arterial pressure}}{\text{cardiac output (millimeters/minute)}}$$

$C_1$, $C_2$ and L are readily calculated.

To accomplish the above, software 50 includes routine 80–82, which comprises a modified Gauss-Newton parameter-estimating algorithm as for the example referenced by Watt and Burrus in their paper entitled, "Arterial Pressure Contour Analysis for Estimating Human Vascular Properties," Journal of Applied Physiology, 1976; 40:171–176, the disclosure of which is hereby incorporated herein by reference. Routines 80–82 calculate the optimal values for coefficients $A_1$–$A_6$, using the measured arterial pressure data as $P_2(t)$. The algorithm uses an iterative approach which preferably provides fast convergence. The algorithm used in routines 80–82 include certain modifications. An automatic stopping procedure is included to stop iteration when an acceptable error level in the curve fitting threshold is reached or when convergence slows below a preset threshold. Also, when the process begins to diverge it returns to the previous best case. The routines also include a weighted iteration interval to improve convergence.

Once the coefficients $A_1$–$A_6$ are established for each pulse contour or waveform, the coefficients are used at routine 84 to calculate the $C_1$, $C_2$, and L vascular impedance parameters for each pulse contour or waveform. $C_1$, $C_2$ and L are all calculated in accordance with the formulas given above. Once calculated for each pulse contour the calculated values are averaged at routine 86, producing mean values more reliable for accuracy than any of the individual values. It shall be understood, however, that the averaging process is not essential. For instance, a median value could be selected for use if desired. At routine 88, the parameters may be stored in storage device 24 or RAM 22 for later retrieval. Finally, routine 90 causes the parameters $C_1$, $C_2$ and L to be displayed on display 18 and/or printed on printer 42.

Alternatively, routine 90 may additionally cause the display or report of cardiac output, mean arterial pressure, heart rate, and a tracing of the blood pressure waveforms.

Thus, the present invention provides an instrument which can noninvasively obtain measures of the modified Windkessel parameters. Accordingly, these parameters can be obtained quickly, inexpensively, easily and without discomfort to the patient, thereby encouraging more widespread beneficial use of the modified Windkessel model parameters in diagnosing, treating and monitoring patients with cardiovascular disease. Also, the vascular impedance measurement instrument provides a ready means to obtain modified Windkessel model parameters for subjects in clinical research trials and laboratory animals used in basic and applied biomedical research projects.

Although the invention has been described with respect to a second order modified Windkessel model of the vasculature, it is applicable to any model of the vasculature based on impedance which is derived from the blood pressure pulse contour of the arterial waveform and cardiac output. As an example, consider the first order model described by Spencer and Denison in "Pulsitile Blood Flow in the Vascular System. The Physiology of the Aorta and Major Arteries," in Hamilton W. F., Dow P. Editors *Handbook of Physiology*, Section 2; circulation, Vol. 2. Washington, D. C. 1963 American Physiological Society, page 799. Spencer ard Denison's RC model treats the arterial system as a simple first-order model which discharges during diastole into a single resistance (the vascular bed). In this model, T=C×R, where T=reciprocal of the exponential slope discharge, C=capacitance, and R=resistance. Therefore, C=T/R.

A number of studies have been conducted using such a first order arterial model, including a number of studies by the French researchers A. Ch. Simon and M. E. Safar. Some of these studies have established normal and abnormal values for the first order parameters C and R, which thus can be used to determine if a patient falls within a normal range or not. Thus, as used in the claims appended hereto, the term "vascular impedance model," shall be inclusive of both the modified Windkessel model, the first order RC arterial model, and any other impedance model of an essentially equivalent nature.

Although the invention has been described herein in its preferred form, those of skill in the art will recognize that many modifications and changes may be made thereto without departing from the spirit and scope of the invention as set forth in the claims appended hereto.

What is claimed:

1. A vascular impedance measurement instrument, comprising:

means for measuring an arterial blood pressure of a patient and producing a corresponding series of digitized data samples representing a waveform of the arterial blood pressure of the patient;

means for determining a mean arterial pressure of the patient from the sample series;

means for determining a cardiac output measurement value for the patient from the sample series and from clinically derived patient data;

means for determining for the patient one or more parameters of a vascular impedance model from the sample series and from the cardiac output value; and means for displaying the one or more parameters.

2. A vascular impedance measurement instrument, comprising:

a sensor that measures an arterial blood pressure of a patient and produces a corresponding series of digitized data samples representing a waveform of the arterial blood pressure of the patient; and a computer operatively coupled to the sensor and configured to:

determine a mean arterial pressure of the patient from the sample series;

determine a cardiac output value for the patient from the sample series and from clinically derived patient data;

determine for the patient one or more parameters of a vascular impedance model from the sample series and from the cardiac output value; and output the one or more parameters.

3. The instrument according to claim 1, wherein the means for measuring comprises:

a pressure transducer; and an analog-to-digital converter operatively coupled to receive a signal from the transducer and to output the sample series.

4. The instrument according to claim 1, wherein the one or more parameters of vascular impedance include a measure of compliance of the patient's blood vessels.

5. The instrument according to claim 4, wherein the one or more parameters of vascular impedance further include a measure of resistance of the patient's blood vessels to the flow of blood.

6. The instrument according to claim 1, wherein the one or more parameters of vascular impedance include a measure of resistance of the patient's blood vessels to the flow of blood.

7. The instrument according to claim 1, further comprising:
   means for marking a segment of the heart beat signal corresponding to systole; and
   means for determining an ejection time by measuring the duration of the segment wherein the determining the cardiac output measurement value is based at least in part on the ejection time.

8. The instrument according to claim 2, wherein the sensor comprises:
   a pressure transducer; and
   an analog-to-digital converter operatively coupled to receive a signal from the transducer and to output the sample series.

9. The instrument according to claim 2, wherein the one or more parameters of vascular impedance include a measure of compliance of the patient's blood vessels.

10. The instrument according to claim 9, wherein the one or more parameters of vascular impedance further include a measure of resistance of the patient's blood vessels to the flow of blood.

11. The instrument according to claim 2, wherein the one or more parameters of vascular impedance include a measure of resistance of the patient's blood vessels to the flow of blood.

12. The instrument according to claim 2, wherein the computer is further configured to mark a segment of the heart beat signal corresponding to systole and determine an ejection time by measuring the duration of the segment, wherein the determination of the cardiac output measurement value is based at least in part on the ejection time.

* * * * *